US00PP29451P2

(12) United States Plant Patent
Van Swieten

(10) Patent No.: US PP29,451 P2
(45) Date of Patent: Jul. 3, 2018

(54) ***PHALAENOPSIS* ORCHID PLANT NAMED 'PHALFONXHE'**

(50) Latin Name: ***Phalaenopsis* hybrid**
Varietal Denomination: PHALFONXHE

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/530,838

(22) Filed: Mar. 6, 2017

(51) Int. Cl.
*A01H 5/02* (2018.01)

(52) U.S. Cl.
USPC ..... Plt./311

(58) Field of Classification Search
USPC ..... Plt./311
See application file for complete search history.

(56) References Cited

PUBLICATIONS

UPOV hit on *Phalaenopsis* plant named 'Phalfonxhe', QZ PBR 20162201, filed Sep. 13, 2016 (Year: 2016).*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALFONXHE', particularly characterized by having light purple flowers with dark red-purple centers, 1 to 4 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFONXHE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFONXHE'.

The new *Phalaenopsis* plant is a product of a planned breeding program conducted by the inventor in Bleiswijk, The Netherlands. The objective of this breeding program was to create a new *Phalaenopsis* plant with light purple flowers and a dark red-purple center, suitable for potted plant production.

The new *Phalaenopsis* plant 'PHALFONXHE' is a result of cross-pollination made by the inventor in October 2006 in Bleiswijk, The Netherlands of the proprietary female, or seed parent, *Phalaenopsis* hybrid '01-1941' (unpatented) with the proprietary male, or pollen parent, *Phalaenopsis* hybrid '22715-03' (unpatented).

The new *Phalaenopsis* was selected by the inventor as a single plant within the progeny of the stated cross-pollination in a controlled greenhouse in Bleiswijk, The Netherlands in October 2009. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFONXHE' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFONXHE' as a new and distinct variety of *Phalaenopsis* plant.

1) Light purple flowers with dark red-purple centers;
2) 1 to 4 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in January 2017. Colors in the photographs may differ from the color values cited in the detailed botanical description, which accurately describe the actual colors of the new variety.

DESCRIPTION OF THE NEW VARIETY

Figure 1:
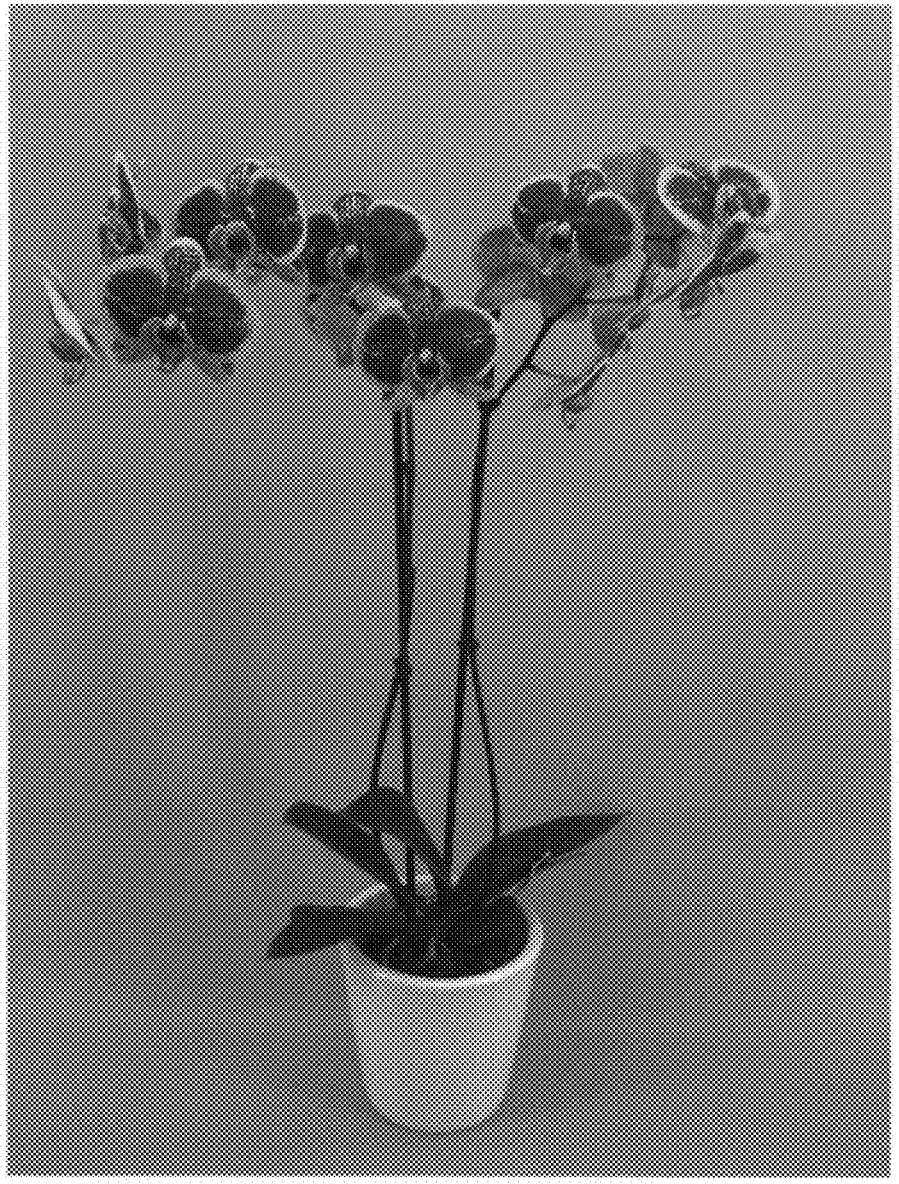
FIG. 1 shows the overall plant habit, including blooms and foliage of 'PHALFONXHE'.
Figure 2:
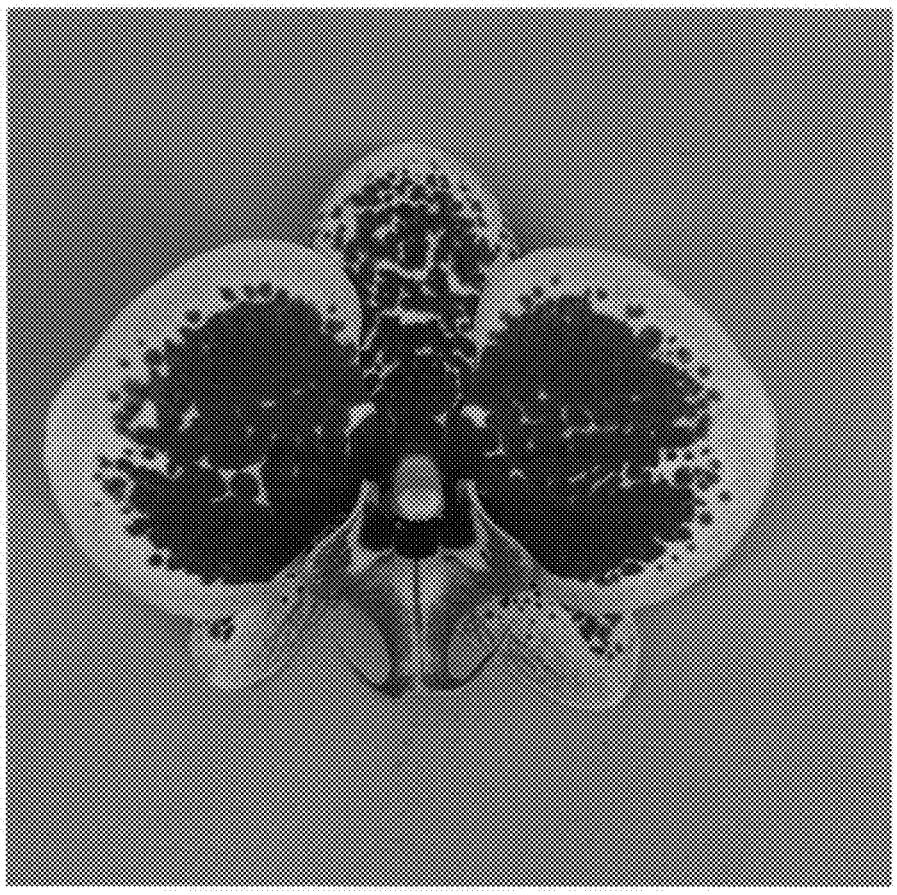
FIG. 2 shows a close-up of a flower of 'PHALFONXHE'.
Figure 3:
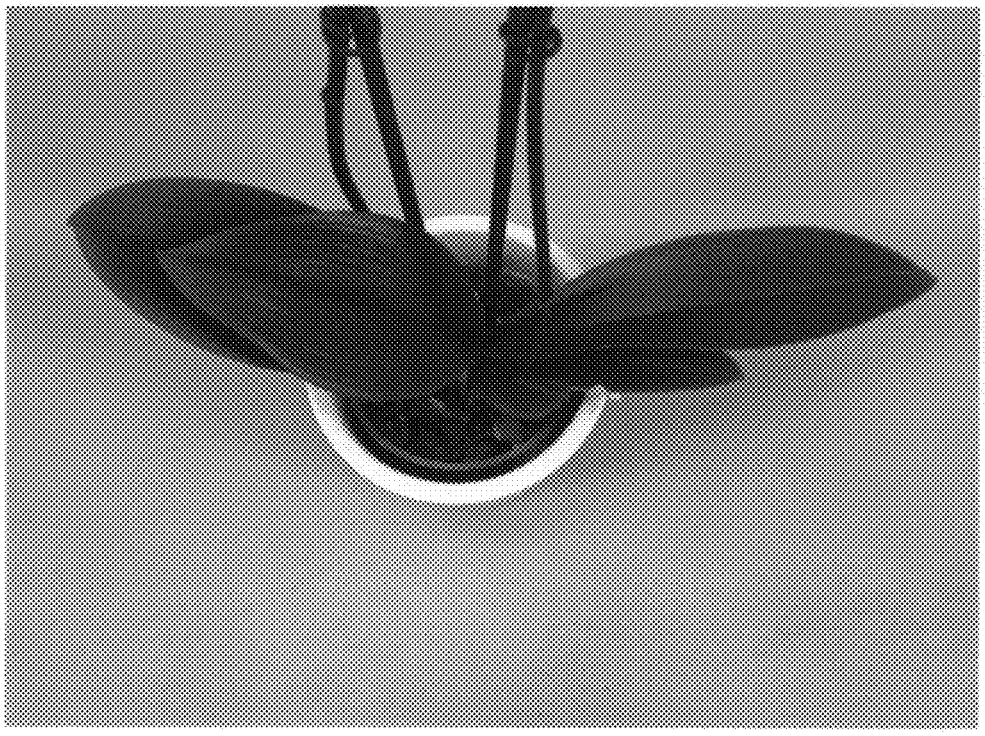
FIG. 3 shows a close-up of the leaves of 'PHALFONXHE'.

The following detailed description sets forth the distinctive characteristics of 'PHALFONXHE'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFONXHE'.

Parentage:

*Female parent*.—*Phalaenopsis* cultivar '01-1941' (unpatented).

*Male parent*.—*Phalaenopsis* cultivar '22715-03' (unpatented).

Propagation:

*Type*.—Meristem tissue culture.

Roots:

*Root description*.—Greyed-green colored roots (RHS 190B/C) with branching lateral roots having greyed red-purple colored root tips (RHS N77B).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 46.0 cm to 56.0 cm.

*Width* (*measured from leaf tips*).—About 35.0 cm to 40.0 cm.

*Vigor*.—Strong.

Leaves:

*Mature leaves*.—Quantity per plant: 6 to 8 leaves are produced before flowering. Length (fully expanded): 15.0 cm to 20.0 cm. Width: 7.0 cm to 8.0 cm. Shape: Oblong. Base shape: Moderately elongated. Apex: Unequal obtuse. Leaf blade angle with the petiole (measured from the horizontal position): Between 15 degrees and 30 degrees. Leaf margin: Entire. Color: Upper surface: RHS 147A. Lower surface: RHS 147B. Texture: Smooth. Thickness: 2.5 mm to 3.0 mm. Venation: Pattern: Parallel. Color of the midvein: Upper surface: RHS 147A. Lower surface: RHS 147B.

Peduncle:

*Quantity per plant*.—1 to 4.

*Number of flowers per peduncle*.—6 to 10.

*Length*.—46.0 cm to 56.0 cm.

*Diameter*.—5.5 mm to 5.8 mm.

*Strength*.—Strong.

*Aspect*.—Upright to slightly pendant.

*Texture*.—Smooth.

*Color*.—Green (RHS 146B) with a touch of brown (RHS 200B).

*Internode length*.—45.0 mm to 50.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 150.0 mm to 180.0 mm.

*Flowering time*.—First flowers can be expected 10 to 11 months after planting in a 12 cm (diameter) pot.

*Flower*.—Height: 65.0 mm to 70.0 mm. Diameter: 80.0 mm to 85.0 mm. Depth of lip: 20.0 mm to 22.0 mm.

*Flower longevity*.—On the plant: 8 to 10 weeks.

*Fragrance*.—Absent.

*Flower bud*.—Average size: Large. Length: 23.0 mm to 25.0 mm. Width: 20.0 mm to 22.0 mm. Shape: Egg shaped. Color: Green (RHS 146D) and red-purple towards the tip (RHS 59B).

*Petals*.—Arrangement: Open/free. Shape: Semi-circular. Apex: Rounded to slightly emarginated asymmetric. Margin: Slightly undulated. Length (from base to tip): 38.0 mm to 40.0 mm. Width: 46.0 mm to 48.0 mm. Color (when fully opened): Upper surface: Basic color: Light purple (RHS 76C). Over color: Dark red-purple (RHS 59B and N79C). Lower surface: Basic color: Light purple (RHS 76D). Over color: Purple (RHS 77D) with diluting dots (RHS N79B).

*Dorsal sepal*.—Shape: Elliptic. Apex: Rounded symmetric. Margin: Entire. Length (from base to tip): 38.0 mm to 40.0 mm. Width: 30.0 mm to 32.0 mm. Color (when fully opened): Upper surface: Basic color: Light purple (RHS 76C). Over color: Dark red-purple spots (RHS 59B and N79C). Lower surface: Basic color: Light purple (RHS 76B). Over color: Light green (RHS 146D) and a touch of purple (RHS N78B).

*Lateral sepals*.—Shape: Ovate. Apex: Obtuse asymmetric. Margin: Entire. Length (from base to tip): 38.0 mm to 40.0 mm. Width: 28.0 mm to 30.0 mm. Color (when fully opened): Upper surface: Basic color: Light purple (RHS 76D). Over color: Dark red-purple spots (RHS 59B and N79C) and purple on the side and tip (RHS N78B). Lower surface: Basic color: Purple (RHS N78B). Over color: Green at the base (RHS 146D); diluting purple spots (RHS N79B).

*Labellum* (*lip*).—Whiskers: Present. Length of whiskers: 14.0 mm to 16.0 mm. Color of whiskers: Purple (RHS N78A) with white edge (RHS NN155C). Pubescence on the lip: Absent. Pubescence on the whiskers: Present.

*Lateral lobe*.—Shape: Spatulate. Margin: Slightly undulated. Length: 20.0 mm to 22.0 mm. Width: 18.0 mm to 20.0 mm. Color: White (RHS NN155C) with purple (RHS N78A) and red-purple (RHS 187B) stripes and small yellow (RHS 4B) spot on the side.

*Apical lobe*.—Shape: Triangular. Margin: Entire. Length: 17.0 mm to 19.0 mm. Width: 20.0 mm to 22.0 mm. Color: Purple (RHS NN78A) and white (RHS NN155C) in the middle toward the tip with light brown (RHS 182C) wings.

*Callus*.—Average size: Medium. Height: 0.6 cm to 0.7 cm. Length: 0.4 cm to 0.5 cm. Width: 0.5 cm to 0.6 cm. Color: Dark red (RHS 187A).

Reproductive organs:

*Column*.—Length: 8.0 mm to 10.0 mm. Diameter: 4.6 mm to 5.1 mm. Color: Light purple (RHS N78C/D).

*Pollinia*.—Quantity: 2. Diameter: 1.0 mm to 1.2 mm. Color: Orange (RHS 25A).

*Ovary*.—Length: 7.0 mm to 9.0 mm. Diameter: 2.1 mm to 2.3 mm.

*Pedicel*.—Length: 28.0 mm to 30.0 mm. Diameter: 2.6 mm to 2.8 mm. Color: Green (RHS 145C) at the base and light purple (RHS N78D) toward the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND SIMILAR COMMERCIAL VARIETIES

'PHALFONXHE' differs from the female parent plant '01-1941' (unpatented), in that 'PHALFONXHE' has light purple flowers with a center pattern and purple (RHS N78A) whiskers with white edge, whereas '01-1941' has white flowers with a spotted pattern and striped edge and red-purple (RHS 71A) whiskers.

'PHALFONXHE' differs from male parent plant '22715-03' (unpatented) in that 'PHALFONXHE' has light purple (RHS 76C) flowers with a center pattern and purple (RHS N78A) whiskers with white edge (RHS NN155C), whereas '22715-03' has purple (RHS N78A) flowers with an even pattern and purple whiskers (RHS N78A).

'PHALFONXHE' is most similar to the commercial *Phalaenopsis* plants named 'PHALFENCK' (U.S. Plant Pat. No. 27,460) and 'PHALFUNWUQ' (unpatented). 'PHALFONXHE' differs from the commercial variety 'PHALFENCK' in that 'PHALFONXHE' has a purple apical lobe with white in the middle toward the tip and light brown wings, and a white lateral lobe with purple and red-purple stripes and small yellow region on one side, whereas 'PHALFENCK' has a red-purple apical lobe that is slightly purple toward the whiskers with a touch of yellow at the base, and a red-purple lateral lobe with a touch of white. Additionally, 'PHALFONXHE' has light purple lateral sepals and purple whiskers with white edge, whereas 'PHALFENCK' has red-purple lateral sepals and red-purple whiskers with yellow tips.

'PHALFONXHE' differs from the commercial variety 'PHALFUNWUQ' in that 'PHALFONXHE' has a purple apical lobe with white in the middle toward the tip and light brown wings, and a white lateral lobe with purple and red-purple stripes and small yellow region on one side, whereas 'PHALFUNWUQ' has a red-purple apical lobe with a touch of purple toward the whiskers, and a purple, dark red and white lateral lobe with dark red fleck toward the base. Additionally, 'PHALFONXHE' has light purple lateral sepals and purple whiskers with white edge, whereas 'PHALFUNWUQ' has red-purple lateral sepals and red-purple whiskers.

I claim:

1. A new and distinct variety of *Phalaenopsis* plant named 'PHALFONXHE', substantially as described and illustrated herein.

* * * * *